United States Patent [19]

Collins et al.

[11] Patent Number: 4,651,718

[45] Date of Patent: Mar. 24, 1987

[54] VERTEBRA FOR ARTICULATABLE SHAFT

[75] Inventors: Ian P. Collins, Welwyn; William J. Revell, Great Dunmow, both of England

[73] Assignee: Warner-Lambert Technologies Inc., Morris Plains, N.J.

[21] Appl. No.: 683,985

[22] Filed: Dec. 20, 1984

[30] Foreign Application Priority Data

Jun. 29, 1984 [GB] United Kingdom ............... 8416587

[51] Int. Cl.$^4$ ............................................... A61B 1/00
[52] U.S. Cl. ......................................... 128/4; 138/120; 350/96.26
[58] Field of Search ........................... 128/4, 3, 5, 6, 7; 138/120; 350/96.26

[56] References Cited

U.S. PATENT DOCUMENTS

| 2,129,391 | 9/1938 | Wappler | 128/6 |
|---|---|---|---|
| 3,190,286 | 6/1965 | Stokes | 128/6 |
| 3,266,059 | 8/1966 | Stelle | 128/4 X |
| 4,290,421 | 9/1981 | Siegmund | 128/6 |

*Primary Examiner*—William H. Grieb
*Attorney, Agent, or Firm*—Alan H. Spencer

[57] ABSTRACT

A shaft which is capable of flexing or articulation under remote control comprises a plurality of identical vertebrae each having a generally circular outer rim (1), an inner hub region (2), and a plurality of webs or spokes (3) interconnecting the outer rim and the inner hub region. The inner hub region presents a projection (6) on one face of the vertebra and a recess (5) on the other face of the vertebra, the projection and recess being of complementary shape and being such that the projections and recesses of adjacent vertebrae arranged in series inter-engage to permit rocking of one vertebra on the adjacent vertebra to provide flexing or articulation. The flexible shaft may form part of an endoscope or other similar medical instrument, or may be the shaft of an industrial instrument such as a bore-scope.

1 Claim, 4 Drawing Figures

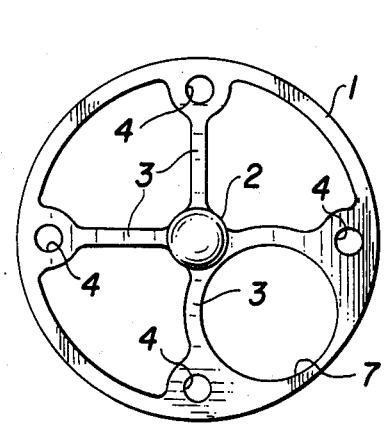
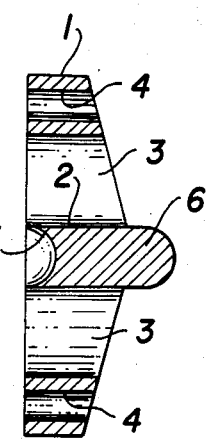
FIG. 1   FIG. 2   FIG. 3
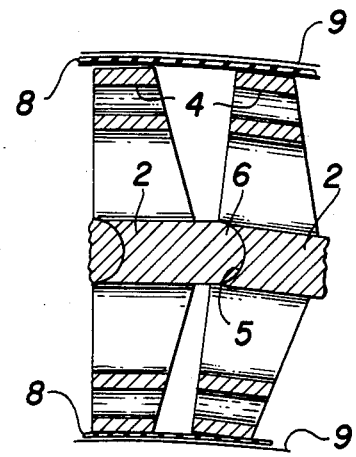
FIG. 4

VERTEBRA FOR ARTICULATABLE SHAFT

FIELD OF THE INVENTION

This invention relates to a vertebra for an articulatable shaft, such as the shaft of an endoscope or borescope, and to a shaft including a plurality of such vertebrae. The term "vertebra" is used because the vertebrae together form the "backbone" of the shaft and enable the latter to articulate.

BACKGROUND TO THE INVENTION

U.S. Pat. No. 4,290,421 discloses a fibrescope having a flexible shaft the distal end of which can be articulated by remote control from a handle of the fibrescope. The distal end of the shaft has a series of vertebrae which are capable of a rocking motion one on the next to enable the distal end of the fibrescope shaft to be articulated. Each vertebra has a central through-bore and a central wire passes through the aligned bores of all the vertebrae to locate the latter. This known form of vertebra has been found to work well, but the present invention aims to provide a modified design of vertebra having particular advantages and not requiring the central wire.

SUMMARY OF THE INVENTION

According to the invention there is provided a vertebra for use with a plurality of identical vertebrae to be arranged in series at one end of a shaft which is capable of flexing or articulation under remote control, the vertebra having a generally circular outer rim, an inner hub region, and a plurality of webs or spokes interconnecting the outer rim and the inner hub region, the inner hub region presenting a projection on one face of the vertebra and a recess on the other face of the vertebra, the projection and the recess being of complementary shape and being such that, when a plurality of vertebrae are arranged in series, the projections and recesses inter-engage to permit rocking of one vertebra on the adjacent vertebra to provide said flexing or articulation.

The projection and recesss are preferably continuous, unbroken part-spherical surfaces, providing a knuckle joint which allows articulation between adjacent vertebrae in any plane. When a plurality of vertebrae are arranged in series, the inter-engagement of the projections and recesses provides lateral location for the vertebra, and it has been found that longitudinal location is adequate without the need for any central wire, as in U.S. Pat. No. 4,290,421. Accordingly, the inner hub region may be devoid of any through-bore or passage, thereby simplifying moulding of the vertebra.

The vertebra may have a circular hole between two adjacent webs or spokes for the passage of a pipe, such as a biopsy pipe in the case of an endoscope. The hole acts to maintain the pipe substantially circular in cross-section and thereby prevents it collapsing to a non-circular shape, which it may be prone to do when the flexible shaft end is bent to a small radius. There may be four webs or spokes, in which case the circular hole is arranged in one quadrant or sector.

On the face of the vertebra presenting the recess, the webs or spokes are preferably co-planar with the rim, and the recess extends inwardly into the inner hub region from this plane. On the other face of the vertebra, the projection preferably projects outwardly beyond the plane of the outer rim to provide the necessary clearance for rocking of one vertebra on another.

The vertebra is conveniently moulded from a rigid low cost plastics material which preferably includes molybdenum disulphide as a minor additive (in amounts up to about 5% by weight) because of its natural lubricating properties.

The invention also includes within its scope a flexible shaft including a plurality of inventive vertebra arranged in series. The shaft may form part of an endoscope or other similar medical instrument, or may be the shaft of an industrial instrument such as a borescope.

The invention will now be further described, by way of example, with reference to the accompanying drawings in which:

FIG. 1 is a view of one face of a vertebra forming the preferred embodiment of the invention, FIG. 2 is a side view of the vertebra of FIG. 1, FIG. 3 is a sectional view of the vertebra of FIGS. 1 and 2, and FIG. 4 is a fragmentary sectional view showing how the vertebrae are arranged in series and are capable of rocking one on the next.

DETAILED DESCRIPTION OF THE DRAWINGS

Referring to FIG. 1, the vertebra is a moulded low cost component which typically has a diameter of about 12 mm making it suitable for inclusion in the distal end of an endoscope shaft. The vertebra has a generally circular outer rim 1, an inner hub region 2 and four webs or spokes 3 interconnecting the outer rim 1 and the hub region 2. At the points where the webs or spokes 3 join the outer rim 1, there are four through-bores 4 to accommodate the four articulation wires (not shown) which effect articulation of the distal end of the endoscope shaft by remote control from the endoscope handle.

On one side of the vertebra (the left hand side as shown in FIGS. 2 and 3), the webs or spokes 3 are co-planar with the outer rim 1, and a hemispherical recess 5 extends inwardly into the hub region 2 from this plane. On the other side of the vertebra the hub region forms a projection 6 having a hemispherical end complementary in shape to the recess 5.

Between two of the webs or spokes 3, the vertebra has a circular hole 7 for receiving, with a sliding fit, a biopsy pipe of the endoscope shaft. Other endoscope functions, such as fibre-optic bundles carrying illuminating light to the distal end of the shaft and an image from the distal end of the shaft, are accommodated in the three other quadrants or sectors defined between the webs or spokes 3 and the outer rim 1.

FIG. 4 shows how a plurality of vertebrae are arranged in series with the projections 6 and recesses 5 interengaging to allow adjacent vertebrae to pivot or rock one on another in any plane, in dependence upon the articulating motion applied to the shaft end by the articulation wires (not shown) passing through the holes 4. FIG. 4 also shows diagrammatically a wire braid 8 which surrounds the series of vertebrae and which is in turn sheathed by an outer covering 9. The biopsy pipe passes through the series of circular holes 7 which act to maintain the cross-section of the biopsy pipe substantially circular, preventing collapse of its wall when the shaft end is articulated to a small radius.

The vertebrae are easily moulded from a rigid low cost plastics material so that they are strong in compression, ensuring uniform overall length of the series of vertebrae. A small amount of molybdenum disulphide (up to about 5% by weight) is added to the plastics material before moulding to improve the natural lubrication properties of the moulded vertebrae.

We claim:

1. A vertebra for use with a plurality of identical vertebrae to be arranged in a series at one end of a shaft which is capable of flexing or articulation under remote control, the vertebra having a generally circular outer rim, an inner hub region, and a plurality of webs or spokes interconnecting the outer rim and the inner hub region, the inner hub region presenting a projection on one face of the vertebra and a recess on the other face of the vertebra, both the projection and the recess having continuous, unbroken surfaces, the projection and the recess being of complementary shape and being such that when a plurality of vertebrae are arranged in a series, the surfaces of said projections and recesses inter-engage to permit rocking of one vertebra on the adjacent vertebra to provide said flexing or articulation, each vertebra comprising a single, unitary, molded plastic piece-part and a circular hole is provided between two adjacent webs or spokes for the passage of pipe, and the hub region is imperforate.

* * * * *